United States Patent [19]

German et al.

[11] Patent Number: 5,763,699
[45] Date of Patent: Jun. 9, 1998

[54] PROCESS FOR PREPARING 2,2-DIPHENYLHEXAFLUOROPROPANES

[75] Inventors: Lev Solomonovich German, deceased, late of Moscow, Russian Federation, by Elena M. German, legal representative; Valerii Romanovich Polishchuk, deceased, late of Lod, Israel, by Margarita Polishchuk, legal representative; Riichi Iwa; Haruyoshi Tatsu, both of Ibaraki, Japan

[73] Assignee: Nippon Mektron, Limited, Tokyo, Japan

[21] Appl. No.: 757,435

[22] Filed: Nov. 27, 1996

Related U.S. Application Data

[62] Division of Ser. No. 544,387, Oct. 10, 1995, abandoned, which is a continuation of Ser. No. 416,014, Apr. 3, 1995, abandoned, which is a continuation of Ser. No. 332,416, Oct. 31, 1994, abandoned.

[30] Foreign Application Priority Data

Oct. 29, 1993 [JP] Japan ..................... 5-294492

[51] Int. Cl.$^6$ ................................. C07C 19/08
[52] U.S. Cl. ........................... 570/127; 570/144
[58] Field of Search ..................... 568/726, 728; 570/127, 144

[56] References Cited

U.S. PATENT DOCUMENTS

| | | | |
|---|---|---|---|
| 3,310,573 | 3/1967 | Gordon | 260/346.3 |
| 4,307,024 | 12/1981 | Kray et al. | 260/389 |
| 4,358,624 | 11/1982 | Mark et al. | 568/722 |
| 4,649,207 | 3/1987 | Lau et al. | |
| 4,758,380 | 7/1988 | Alston et al. | |
| 4,774,370 | 9/1988 | Schneider et al. | |
| 5,288,908 | 2/1994 | Lau et al. | |

FOREIGN PATENT DOCUMENTS 0 092 310  10/1983  European Pat. Off.

OTHER PUBLICATIONS

*Chemical Abstracts*, vol. 97, No. 22, Nov. 29, 1992, pp. 2381–2393, Abstract No. 182895.

Syntheses of Polymer Intermediates Containing The Hexafluoroisopropylidene Group via Functionalization of 2,2-Diphenylhexafluoropropane, K.S.Y. Lau et al. (1982).

Izv. Akad. Nauk. USSR Ser. Khim. No. 3, p. 614, 1967.

Ibid. No. 4, p. 683, 1960.

*Primary Examiner*—C. Warren Ivy
*Assistant Examiner*—Lymon H. Smith
*Attorney, Agent, or Firm*—Barnes & Thornburg

[57] ABSTRACT

2,2-diphenylhexafluoropropanes are prepared by condensation reaction of benzene or benzenes substituted with a halogen atom or atoms, a lower alkyl group or groups or a hydroxyl group or groups with hexafluoroacetone in the presence of trifluoromethane sulfonic acid. Among the 2,2-diphenylhexafluoropropanes, 2,2-diphenylhexafluoropropane and 2,2-bis(p-chlorophenyl)hexafluoropropane are novel compounds.

2 Claims, No Drawings

PROCESS FOR PREPARING 2,2-DIPHENYLHEXAFLUOROPROPANES

This is a Divisional of application Ser. No. 08/544,387 filed Oct. 10, 1995, now abandoned; which is a Continuation of application Ser. No. 08/416,014 filed Apr. 3, 1995, now abandoned; which is a Continuation of application Ser. No. 08/332,416 filed Oct. 31, 1994, now abandoned.

BACKGROUND OF THE INVENTION

1. Field of the Invention

The present invention relates to a process for preparing 2,2-diphenylhexafluoropropanes, and more particularly to a process for preparing 2,2-diphenylhexafluoropropanes by condensation reaction of benzene or substituted benzene with hexafluoroacetone.

2. Description of the Prior Art

Heretofore, 2,2-diphenylhexafluoropropanes as intermediates for medicines, agricultural chemicals, etc., or intermediates for synthetic rubber vulcanizing agents have been prepared by condensation reaction of benzene or substituted benzene with hexafluoroacetone in the presence of hydrofluoric acid. However, the condensation reaction is effective only for lower alkyl-substituted or hydroxyl-substituted benzenes, and the reaction fails to proceed in case of benzene or halogen-substituted benzenes. That is, two-stage reaction has been required for the halogen-substituted benzenes [Izv. Akad. Nauk. USSR Ser. Khim. No.3, page 614 (1967); ibid. No.4, page 683 (1960)].

SUMMARY OF THE INVENTION

An object of the present invention is to provide a process for preparing various 2,2-diphenylhexafluoropropanes by condensation reaction of benzene or benzenes substituted with a wide range of substituents with hexafluoroacetone.

DETAILED DESCRIPTION OF THE INVENTION

According to the present invention 2,2-diphenylhexafluoropropanes are prepared by condensation reaction of benzene or benzenes substituted with a halogen, a lower alkyl group having 1 to 5 carbon atoms or a hydroxyl group with hexafluoroacetone in the presence of trifluoromethane sulfonic acid. When a substituted benzene is used, the number of the substituents is usually 1 and can be 2 or more.

Benzene or substituted benzenes such as monofluorobenzene, monochlorobenzene, monobromobenzene, toluene, o-xylene, ethylbenzene, cumene, hydroxybenzene, etc. and hexafluoroacetone are used usually in a molar ratio of the former to the latter of 2:1. In the condensation reaction gaseous hexafluoroacetone is used, and thus it is usually preferable to use a pressure vessel such as an autoclave, etc. The condensation reaction can be also carried out by passing more than a stoichiometrical amount of hexafluoroacetone through the reaction solution while keeping the hexafluoroacetone in a gaseous state. Reaction temperature is usually in a range of about 0° to about 300° C., preferably about 0° to about 200° C.

According to an actual embodiment of condensation reaction, benzene or substituted benzenes and trifluoromethane sulfonic acid are charged into a reactor vessel, and then hexafluoroacetone is filled therein or passed therethrough, where usually an excess amount of trifluoromethane sulfonic acid is used so that about 1.2 to about 1.6 parts by mole of trifluoromethane sulfonic acid can be present per part by mole of hexafluoroacetone. Other perfluoroalkane sulfonic acids than trifluoromethane sulfonic acid can be used.

After the reaction, the desired product can be recovered from the resulting reaction solution according to a conventional procedure, for example, by methylene dichloride extraction, solvent distillation, etc. when a mono-substituted benzenes are used, 2,2-bis(p-substituted phenyl) hexafluoropropanes can be obtained. When benzene or chlorobenzene is subjected to reaction with hexafluoroacetone, 2,2-diphenylhexafluoropropanes of the following general formula, where X are a hydrogen atom or a chloride atom, can be obtained, and these compounds are novel compounds:

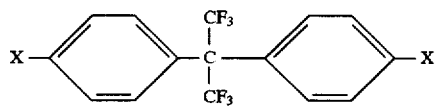

By using trifluoromethane sulfonic acid $CF_3SO_3H$ as a dehydrating-condensing agent, benzene or halogenobenzenes, which has undergone no condensation reaction so far according to the conventional process, can undergo condensation reaction to produce various 2,2-diphenylhexafluoropropanes.

Substituents on phenyl groups of the resulting 2,2-diphenylhexafluoropropanes can be further converted to other groups. For example, halogen on the phenyl groups can be converted to nitrile groups upon reaction with CuCN, and the resulting compounds can be used as raw materials for polybenzoxazole, etc. as heat-resistant resins. Methyl groups on the phenyl groups can be converted to carboxyl groups upon oxidation with $KMnO_4$, and the resulting compounds can be used also as raw materials for aromatic polyamide and aromatic polyimide as heat-resistant resins.

PREFERRED EMBODIMENTS OF THE INVENTION

The present invention will be explained in detail below, referring to Examples.

EXAMPLE 1

3.9 g (50 mM) of benzene and 4.5 g (30 mM) of $CF_3SO_3H$ were charged into an autoclave having a net capacity of 20 ml, and then 4.2 g (25 mM) of hexafluoroacetone was filled therein. The autoclave was stirred for two hours while heating it at 100° C. After the end of reaction, the autoclave was cooled, and the resulting reaction mixture was poured into ice water and subjected to extraction with methylene dichloride three times. Liquid extract was washed with water three times, then washed and neutralized with an aqueous sodium hydrogen carbonate solution, and dried over magnesium sulfate. The solvent was removed from the solution by distillation, and the residues were subjected to distillation under reduced pressure, whereby 5.1 g of 2,2-diphenylhexafluoropropane having a boiling point of 89°–90° C./3 mmHg was obtained (yield: 67%).

The product was analyzed. A singled peak was found at −14.2 ppm (chemical shift) by $^{19}F$-NMR and 1H peak was found at 7.06 ppm, a 2H peak at 7.08 ppm and a 2H peak at 7.47 ppm by integral by $^1H$-NMR (integrated), and the product was indentified to be the desired product.

EXAMPLE 2

Reaction was carried out at 100° C. for 8 hours in the same manner as in Example 1, except that 4.8 g (50 mM) of monofluorobenzene was used in place of benzene, whereby 4.3 g of 2.2-bis-(p-fluorophenyl)hexafluoropropane having a boiling point of 84°–85° C./4 mmHg was obtained (yield: 50%).

$^{19}$F-NMR: −14.2 ppm($CF_3$), 33.9 ppm(F)

$^1$H-NMR: 6.71 ppm, 7.17 ppm(aromatic nucleus H)

EXAMPLE 3

Reaction was carried out at 115° C. for 4 hours in the same manner as in Example 1, except that 4.7 g (50 mM) of phenol was used in place of benzene. Solid product having a melting point of 160.5°–161.5° C. obtained by crystalization without distillation was analyzed and identified to be 2.2-bis(p-hydroxyphenyl)hexafluoropropane, where the amount of the product was 8.0 g (yield: 95%).

$^{19}$F-NMR: −13.7 ppm $^1$H-NMR: 3.7 ppm(—OH), 7.46 ppm(aromatic nucleus 2H), 6.44 ppm(aromatic nucleus 2H)

EXAMPLE 4

Reaction was carried out at 185° C. for 12 hours in the same manner as in Example 1, except that 5.63 g (50 mM) of monochlorobenzene was used in place of benzene, whereby 7.7 g of 2.2-bis-(p-chlorophenyl)hexafluoropropane having a boiling point of 129°–130° C./4 mmHg and a melting point of 53°–54° C. was obtained (yield: 83%).

Mass spectra: 372 ($M^+$), 353 ($M^+$—F), 337 ($M^+$—Cl), 303 ($M^+$—$CF_3$), 268($M^+$—Cl—$CF_3$), 248 ($M^+$—Cl—$CF_3$—HF)

$^{19}$F-NMR: −13.8 ppm($CF_3$)

$^1$H-NMR: 7.06 ppm

EXAMPLE 5

8.6 g (94 mM) of toluene and 12.0 g (80 mM) of $CF_3SO_3H$ were charged into a reactor vessel having a net capacity of 50 ml, provided with a condenser, and a hexafluoroacetone gas was passed through the liquid reaction mixture over 9 hours. Then, the reaction mixture was refluxed for 2 hours, cooled and poured into ice water, followed by extraction with methylene dichloride three times.

Then, the extract was washed with water three times, washed and neutralized with an aqueous sodium hydrogen carbonate solution, and dried over magnesium sulfate. The solvent was moved from the solution by distillation, and 14.5 g of 2.2-bis(p-methylphenyl)hexafluoropropane having a purity of 95% and a melting point of 76°–77° C. was obtained as the residues (yield: 93%).

Mass spectra: 332($M^+$), 327 ($M^+$—$CH_3$), 313 ($M^+$—F), 263($M^+$—$CF_3$), 248 ($M^+$—$CF_3$—HF), 228($M^+$—$CF_3$—$CH_3$—HF), 193($M^+$—2$CH_3$—H), 179($M^+$—2$CF_3$—$CH_3$)

$^{19}$F-NMR: —14.1 ppm ($CF_3$)

$^1$H-NMR: 2.11 ppm($CH_3$), 6.95 ppm (aromatic nucleus 2H), 7.47 ppm(aromatic nucleus 2H)

What is claimed is:

1. A process for producing 2.2-diphenylhexafluoropropanes having the general formula:

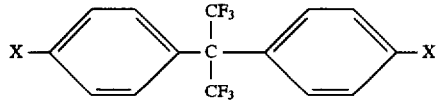

wherein x is a hydrogen atom or a halogen atom, which process comprises:

subjecting benzene or monohalogenated benzene to a condensation reaction with hexafluoroacetone in the presence of trifluoromethane sulfonic acid.

2. The process for producing 2.2-diphenylhexafluoropropanes according to claim 1, wherein the benzene or monohalogenated benzene and hexafluoroacetone are used in a molar ratio of 2:1.

* * * * *